US008828909B1

(12) United States Patent
Fabry et al.

(10) Patent No.: US 8,828,909 B1
(45) Date of Patent: Sep. 9, 2014

(54) COMPOSITIONS FOR PROTECTING GENETICALLY ENGINEERED PLANTS FROM DISEASE AND PHYTOTOXIC EFFECTS OF HERBICIDES

(71) Applicant: Plant Food Systems, Inc., Zellwood, FL (US)

(72) Inventors: Carl J. Fabry, Orlando, FL (US); Paul E. Fabry, Winter Garden, FL (US)

(73) Assignee: Plant Food Systems, Inc., Zellwood, FL (US)

( * ) Notice: Subject to any disclaimer, the term of this patent is extended or adjusted under 35 U.S.C. 154(b) by 0 days.

(21) Appl. No.: 13/836,072

(22) Filed: Mar. 15, 2013

Related U.S. Application Data

(60) Continuation-in-part of application No. 13/097,032, filed on Apr. 28, 2011, now abandoned, and a continuation-in-part of application No. 13/538,661, filed on Jun. 29, 2012, now Pat. No. 8,461,079, which is a continuation-in-part of application No. 13/094,932, filed on Apr. 27, 2011, now Pat. No. 8,216,972, which is a continuation-in-part of application No. 13/035,779, filed on Feb. 25, 2011, now Pat. No. 8,193,119, said application No. 13/538,661 is a continuation-in-part of application No. 13/308,681, filed on Dec. 1, 2011, now Pat. No. 8,221,516, said application No. 13/097,032 is a continuation-in-part of application No. 13/019,564, filed on Feb. 2, 2011, now Pat. No. 8,088,191, which is a division of application No. 11/349,064, filed on Feb. 6, 2006, now Pat. No. 7,887,616.

(60) Provisional application No. 61/308,569, filed on Feb. 26, 2010, provisional application No. 60/650,378, filed on Feb. 4, 2005, provisional application No. 61/308,684, filed on Feb. 26, 2010.

(51) Int. Cl.
*A01N 59/00* (2006.01)

(52) U.S. Cl.
USPC .......................................................... 504/119

(58) Field of Classification Search
None
See application file for complete search history.

(56) References Cited

U.S. PATENT DOCUMENTS

| | | |
|---|---|---|
| 3,171,733 A | 3/1965 | Hignett et al. |
| 3,464,808 A | 9/1969 | Kearns |
| 3,853,530 A | 12/1974 | Franz |
| 3,950,495 A | 4/1976 | Ries |
| 3,977,860 A | 8/1976 | Franz |
| 3,985,538 A | 10/1976 | Hicks et al. |
| 4,601,891 A | 7/1986 | McGill et al. |
| 4,637,921 A | 1/1987 | Sansing et al. |
| 4,724,132 A | 2/1988 | Fabry |
| 5,736,164 A | 4/1998 | Taylor |
| 5,800,837 A | 9/1998 | Taylor |
| 5,925,383 A | 7/1999 | Taylor |
| 5,997,910 A | 12/1999 | Taylor |
| 6,338,860 B1 | 1/2002 | Taylor |
| 6,509,041 B2 | 1/2003 | Taylor |
| 6,541,424 B2 | 4/2003 | Roberts et al. |
| 2001/0051591 A1* | 12/2001 | Ferrett et al. ............ 504/103 |
| 2006/0159772 A1 | 7/2006 | Garavaglia |

FOREIGN PATENT DOCUMENTS

CN 101601407 * 12/2009

OTHER PUBLICATIONS

Scroggs, Derek M., et al., "Glyphosate Efficacy on Selected Weed Species is Unaffected by Chemical Coapplication"; Weed Technology, vol. 19, No. 4 (Oct.-Dec. 2005), pp. 1012-1016 Abstract.
Derek M Scroggs, Donnie K. Miller, James L. Griffin, James P. Geaghan, P. Roy Vidrine and Alexander M. Stewart; Glyphosate Efficacy on Selected Weed Species is Unaffected by Chemical Coapplication; Weed Technology, vol. 19, No. 4 (Oct.-Dec. 2005), pp. 1012-1016 Abstract.
Roundup Power Max product literature, Monsanto Company, St. Louis, MO (2010).

* cited by examiner

*Primary Examiner* — Alton Pryor
(74) *Attorney, Agent, or Firm* — Potter Anderson Corroon LLP; Hilmar L. Fricke, Esq.

(57) ABSTRACT

The composition provides herbicidal, fungicidal and/or nutritional activity to genetically engineered crops in a single application and comprises an aqueous composition of:
(1) a glyphosate salt; and,
(2) a phosphite selected from the group consisting of: potassium phosphite, potassium polyphosphite or any combinations; and,
wherein the molar ratio of (1) to (2) is about 1:4 to about 1:1 and where the concentration of (1) is applied at the rate of between 0.47-4.13 lbs/acre.

7 Claims, No Drawings

COMPOSITIONS FOR PROTECTING GENETICALLY ENGINEERED PLANTS FROM DISEASE AND PHYTOTOXIC EFFECTS OF HERBICIDES

FIELD OF THE INVENTION

The present disclosure relates to compositions that protect crops of genetically engineered plants from the phytotoxic effects of herbicides, such as, glyphosates, that are applied to these crops for the reduction of growth of unwanted vegetation; thereby, mitigating damage to the non-target plants.

BACKGROUND OF THE INVENTION

Various elemental Phosphorus (P) derivatives and methods are, known in the chemical art as "glyphosates", which are effective and commercially important broad spectrum herbicides useful in controlling the growth of geminating seeds, emerging seedlings, maturing and established woody and herbaceous vegetation and aquatic plants.

Glyphosates are used as post-emergent herbicides to control the growth of a wide variety of weed species in crops and are the active ingredient in the "ROUNDUP" family of herbicides available from Monsanto Company, (St. Louis, Mo. Glyphosates have been widely used in agriculture for many years and the preparation and use thereof are disclosed in U.S. Pat. Nos. 3,853,530 and 3,977,860.

Beneficial plants have been genetically engineered to resist or tolerate glyphosates and crops of such plants are treated with glyphosates usually by spray application to reduce or eliminate adjoining weeds and other harmful vegetation which reduce crop yields.

Advances in genetic engineering have transformed cultivated crops, such as, soybeans, maize (corn), sorghum, canola, alfalfa, cotton and wheat to provide tolerance to glyphosate herbicides, also known as "ROUNDUP READY" crops.

Glyphosate resistant or tolerant crops reduce the need for tillage for weed control thereby reducing soil erosion and lowering crop production costs (fuel and labor) involved in tillage. However, for many crops, the genetically induced resistance is not completely total, and the application (usually foliar) of the glyphosate, can result in yield losses since the crop may also be adversely affected, either mildly or greatly, by the herbicide application. Depending on other adverse factors of production, such as, soil conditions, climate, disease, insect pressure, inadequate plant nutrition, or other factors, the crop can itself be temporarily stunted from the herbicide application and suffer a "set back", or "yield drag" from which it takes time to recover.

As used herein, the term "yield drag" is defined as the decrease in crop yield as a result of applying increasing rates of a glyphosate herbicide such as Roundup to genetically engineered Roundup Ready crops in order to mitigate weed growth.

As used herein, the term "set back" is defined as the decline in physical appearance and vigor of a genetically engineered Roundup Ready crop resulting from the Roundup application itself.

It is during this recovery period that crops are weakened and vulnerable to other forms of crop reduction pressure, before a return to a normal growth pattern. In many cases the plants may not fully recover which results in a reduced crop yield.

An inadequate method to avoid this "set back" or "yield drag" is to use/precscribe lower rates of glyphosphate so that the adverse effect to the crop is reduced, but this can result in inadequate weed control and the development of glyphosate resistant weed species.

It would be desirable to have a composition that when applied with herbicides would allow genetically engineered crops to avoid such "set back" or "yield drag" losses altogether or at least allow them to recover more quickly after application of glyphosate and other herbicides in order to improve crop yields as well as improve the health of the crop.

It would further be desirable to have a product that can be applied to genetically engineered food crops that will both control undesirable and unwanted vegetation, but also effectively stop, retard, or mitigate fungal and bacterial diseases, and/or insect crop damage, caused by, or exacerbated by foliar herbicide applications.

It would further be desirable to have a product that can be applied together with the glyphosate in order to allow the glyphosate to be applied at full strength in order to control resistant and non-resistant weed species while not harming or reducing the yield of the desirable or planted crop.

SUMMARY OF THE INVENTION

The composition of this invention provides protection against set-back to genetically engineered crops resistant to the effects of a glyphosate herbicide and improves crop yields.

The novel composition of this invention combines salts of glyphosate with a phosphite in effective amounts for foliar application to genetically engineered crops. The effective amount of glyphosate continues to be a weed control composition, while the effective amount of the phosphite eliminates or substantially reduces the set back period of time, allowing crops to meet their genetic growth potential to grow healthier and result in crop yields being higher in a shorter period of time than if a dissolved glyphosate salt solution was applied individually.

The composition of this invention comprises:
(1) glyphosate salt; and,
(2) phosphite wherein the molar ratio of (1) to (2) is about 1:2 to about 4:1, and more preferably, about 1:1 to 2:1 and,
where (1) and (2) are provided in a diluted solution in which the amount of glyphosate salt in solution is applied at the rate of about 0.47 lbs/acre to about 4.13 lbs/acre.

In one embodiment of the invention, the glyphosate salt is dissolved to form a concentrated solution or can be purchased in a product such as ROUNDUP POWER MAX®. It is thereafter diluted and the phosphite component is added to the diluted solution prior to foliar application.

DEFINITIONS

The term "about" means within 10% of a given value or range.

The term "comprising" is intended to include embodiments encompassed by the terms "consisting essentially of" and "consisting of". Similarly, the term "consisting essentially of" is intended to include embodiments encompassed by the term "consisting of".

The term "phosphite" means salts of phosphorous acid, whose mono- and di-basic salts include mono- and di-potassium, mono- and di-sodium, mono- and di-ammonium, or combinations thereof. In addition, phosphorous acid molecules can be joined by a condensation reaction to form a series of polyphosphorous acids, and polyphosphite salts. These polyphosphite salts include mono- and di-potassium, mono- and di-sodium, mono- and di-ammonium.

The term "glyphosate" means salts of N-(phosphonomethyl)glycine such as, ammonium salt, e.g. diammonium salt, amine salt, e.g. isopropyl amine salt, potassium salt, sodium salt, or sulfonium salt, e.g. trimethyl sulfonium salt or combinations thereof.

The term "genetically engineered crops" means crops or plants, such as, soybeans, maize (corn), sorghum, canola, alfalfa, cotton and wheat that have been genetically engineered to provide tolerance to a glyphosate or other herbicides. Crops described as Roundup Ready are included under this term.

Phosphites are effective because they are systemic fungicides which, unlike surface protectant fungicides which can easily wash off the plant surface, can protect plants from diseases during the entire growing season. Phosphites move systemically upward and downward throughout the entire plants vascular system, translocating to the new growth, via both the xylem and the phloem activating the plants own natural, self defense mechanisms, systemic acquired resistance (SAR) and induced resistance (IR).

Calculations are based upon ROUNDUP POWER MAX® which provides 5.5 pounds potassium salt of glyphosate per US gallon. Based on the concentration of glyphosate salt in POWER MAX®, a foliar application of 11 oz/acre of ROUNDUP POWER MAX® equates to 0.47 pounds of glyphosate salt per acre and application of 96 oz/acre equates to 4.13 pounds dissolved glyphosate salt per acre.

Over this range, i.e. 11 oz/acre to about 96 oz/acre, genetically engineered plants are surprisingly tolerant in view of the glyphosate manufacturer's warning not to exceed 44 oz/acre (1.89 lbs/acre). The addition of phosphite to the glyphosate salt solution subsequently diluted and then foliar applied to genetically engineered plants improves the health of the plant while providing effective weed control up to at least six weeks after application.

Delivery of a higher concentration of glyphosate in the form of a glyphosate salt solution means that significant weed development is less likely to occur prior to harvest. It is believed that foliar application of a greater amount of glyphosate salt minimizes the potential that weeds will develop a resistance to treatment as may occur if treatment is delivered in repetitive smaller doses over time. By saving at least one extra trip across the field, the combining of effective amounts of dissolved glyphosate salt and phosphite reduces labor costs and is more environmentally friendly. As mentioned earlier, the glyphosate salt phosphite combination also synergistically reduces yield drag and set back to genetically engineered crops than if a glyphosate salt solution was applied separately. The glyphosate herbicide component provides effective weed control while the phosphite component provides the necessary stimulus to maintain vigorous growth.

The novel composition of glyphosate salt and phosphite can be cold blended with water for application. The composition may also be used in a concentrated form for metering and injection for crop application. Typically, effective amounts are applied to a crop depending on the crop and the result that is required.

The novel composition can be pre-blended for simultaneous application either as a pre-blended stable, clear and sprayable product composition having a relatively long shelf life; or, tank mixed together in the field for application.

In one embodiment, an aqueous potassium polyphosphite solution is the phosphite component prepared by a process set forth in U.S. Pat. No. 7,887,616 and which is hereby incorporated by reference.

Another preferred embodiment is a composition that when applied to genetically engineered crops the composition provides the crops resistance to set-back and consists essentially of a glyphosate and a phosphite; wherein the molar ratio of glyphosate to phosphite is about 1:2 to about 4:1, and more preferably, from 1:1 to 2:1 and the concentration range for foliar application of glyphosate salt is between about 0.47 lbs/acre (11 oz/acre) and 4.13 lbs/acre (96 oz/acre).

With respect to the phosphite used, calculations in this specification are based upon a dissolved phosphite solution of KPHITE®, manufactured by Plant Food Systems, Zellwood, Fla. which provides 7.03 pounds of phosphite (mono- and dipotassium salts of phosphorus acid) dissolved in one gallon of liquid.

Any of the embodiments presented herein or made according to our invention can be diluted with water for agricultural treatment of Round-up Ready crops or other genetically engineered crops. Additional nutrients well known in the agriculture industry can also be added to the diluted solution for foliar application

DETAILED DESCRIPTION OF THE PREFERRED EMBODIMENT

By combining phosphite with a salt of glyphosate, "set back" of genetically engineered crops can be substantially reduced or eliminated.

Genetically engineered crops, specifically Roundup Ready corn, cotton and soybeans were seeded in 36" rows; each row being 60 feet in length. Between each Roundup Ready row was seeded respective rows of Johnsongrass, Sicklepod, Ragweed and Pigweed. The plants were allowed to germinate and the foliar test application began 42 days after planting.

Fifteen separate treatments were applied, three replications per treatment; each treatment covering 3 ft of each row and the treatments were applied perpendicularly across each row. Between each application was a 1 foot spacing to minimize comingling of treatments.

The glyphosate salt used in the testing was a product sold under the trademark ROUNDUP POWER MAX®, a product manufactured by Monsanto Chemical, St. Louis, Mo. The active ingredient was Glyphosate, N-(phosphonomethyl)glycine, in the form of its potassium salt making up 48.7% of the solution. ROUNDUP POWER MAX contains 660 grams per liter or 5.5 pounds per US gallon of the active ingredient glyphosate. The application rate of ROUNDUP POWER MAX® was tested at 11 oz, 22 oz, 32 oz, 44 oz, 64 oz and 96 oz/acre diluted with water.

The phosphite component used for testing was a product sold under the trademark KPhite® 7LP, a product manufactured by Plant Food Systems, Inc., Zellwood, Mo. The KPhite® product has as active ingredients mono and di potassium phosphite making up about 56.0% of the solution and contains 7.03 pounds per US gallon of the active ingredients.

The phosphite solution was combined with the glyphosate salt solution and applied to the plants at an application rate of 32 oz/acre.

TABLE 1

Roundup Ready Trial (42 day evaluation)

| Treatment | Description | Weed Control Effectiveness | Crop Appearance |
|---|---|---|---|
| 1 | 11 oz Roundup Power Max | 2.5 | 8 |
| 2 | 11 oz Roundup Power Max + 32 oz Kphite | 2.5 | 10 |
| 3 | 22 oz Roundup Power Max | 4 | 7 |

TABLE 1-continued

Roundup Ready Trial (42 day evaluation)

| Treatment | Description | Weed Control Effectiveness | Crop Appearance |
|---|---|---|---|
| 4 | 22 oz Roundup Power Max + 32 oz Kphite | 4 | 10 |
| 5 | 32 oz Roundup Power Max | 5 | 6 |
| 8 | 32 oz Roundup Power Max + 32 oz Kphite | 5 | 10 |
| 7 | 1 qt Kphite | 1 | 10 |
| 8 | Untreated Check | 1 | 9 |
| 9 | 44 oz Roundup Power Max | 6 | 4 |
| 10 | 44 oz Roundup Power Max + 32 oz. Kphite | 6 | 9 |
| 11 | 64 oz Roundup Power Max | 7 | 3.5 |
| 12 | 64 oz Roundup Power Max + 32 oz. Kphite | 7 | 8 |
| 13 | 96 oz Roundup Power Max | 9 | 2 |
| 14 | 96 oz Roundup Power Max + 32 oz. Kphite | 9 | 7 |

Rating Scale of 1 to 10 with 1 = Poor and 10 = Excellent

Test Results 42 days following foliar application, the plants were observed. A scale of 1 to 10 was used for rating weed control effectiveness and crop appearance. Both the weed control effectiveness of the foliar application and the crop appearance were visually observed and each assigned a value.

Crop appearance is a visual observation comparing each treatment against how a crop should appear. The phosphite-only treatment had the best appearance, i.e. no set back and no yield drag (Test 7).

The maximum foliar application rate was 96 oz/acre ROUNDUP POWER MAX® (Tests 13 and 14). The appearance of genetically engineered crops were surprisingly healthier when applied in combination with phosphite (Test 14) than crops receiving only the glyphosate salt solution (Test 13). Lower application rates of ROUNDUP (Tests 1, 3, and 5), exhibited noticeable deterioration of crop appearance when compared to the untreated sample (Test 8).

At low concentrations of ROUNDUP (Tests 2, 4, and 6), no set back or yield drag was observed. However, the level of weed control, as expected, greatly improved at the higher application rates of ROUNDUP POWER MAX. The lowest application rate of ROUNDUP POWER MAX (test 1) showed poor weed control and limited crop injury.

From the above testing, the following conclusions are presented:

A. Use of a glyphosate salt solution as a single application causes Roundup Ready Crops to suffer set-back and the degree of set-back is proportional to the concentration applied.

B. The co-application of a glyphosate salt solution and a phosphite component showed surprising and unexpected results. The phosphite component, although applied at a single application rate (32 oz/Acre) had a beneficial effect to genetically engineered crops experiencing no set-back regardless of the dissolved glyphosate salt application rate (11 oz/Acre-96 oz/Acre).

What is claimed is:

1. A composition that provides weed control and reduces set back to genetically engineered crops comprising:
   (1) a glyphosate selected from the group consisting of: ammonium salt, diammonium salt, amine salt, isopropyl amine salt, potassium salt, sodium salt, and any combinations thereof; and
   (2) a phosphite selected from the group consisting of: mono-potassium phosphite and di-potassium phosphite, mono-sodium phosphite, di-sodium phosphite, mono-ammonium phosphite, di-ammonium phosphite, and any combination thereof;
   wherein the molar ratio of (1) to (2) is about 1:1 to about 4:1; and
   wherein (1) and (2) are provided in a diluted solution in which the amount of glyphosate salt in solution is applied to the genetically engineered crops at the rate of between about 64 oz/acre to about 96 oz/acre and
   wherein said composition is effective in controlling weed growth and enhancing the physical appearance in genetically engineered crops.

2. The composition of claim 1 in the form of a concentrate for metering into an aqueous spray for foliar application.

3. The composition of claim 1 in the form of an aqueous premixed blend for direct foliar application to the crop.

4. A method of treating a plant genetically engineered to be resistant to an herbicide, the method comprising applying an effective amount of the composition of claim 1.

5. The method of claim 4 in which said plant genetically engineered is selected from the group consisting of: soy bean, maize, sorghum, canola, alfalfa, cotton or wheat.

6. A composition for foliar application to genetically engineered crops consisting essentially of:
   (1) a glyphosate selected from the group consisting of: ammonium salt, diammonium salt, amine salt, isopropyl amine salt, potassium salt, sodium salt, and any combinations thereof;
   (2) a phosphite selected from the group consisting of: mono-potassium phosphite and di-potassium phosphite, mono-sodium phosphite, di-sodium phosphite, mono-ammonium phosphite, di-ammonium phosphite, and any combinations thereof; and
   wherein the molar ratio of (1) to (2) is about 1:1 to about 4:1; and
   wherein said (1) and (2) are combined with a use-effective amount of water and thereafter applied to genetically engineered crops, the amount of (1) is applied at the rate of between about 64-about 96 ounces per acre and
   wherein said composition is effective in controlling weed growth and enhancing the physical appearance in genetically engineered crops.

7. A foliar application comprising:
   (1) a glyphosate selected from the group consisting of: ammonium salt, diammonium salt, amine salt, isopropyl amine salt, potassium salt, sodium salt, and any combinations thereof; and
   (2) a phosphite selected from the group consisting of: mono-potassium phosphite and di-potassium phosphite, mono-sodium phosphite, di-sodium phosphite, mono-ammonium phosphite, di-ammonium phosphite, and any combination thereof;
   wherein the molar ratio of (1) to (2) is about 1:1 to about 4:1; and
   wherein (1) and (2) are combined with a use-effective amount of water and thereafter applied to genetically engineered plants in which the amount of glyphosate salt is from about 64 oz/acre to about 96 oz/acre and
   wherein said composition is effective in controlling weed growth and enhancing the physical appearance in genetically engineered crops.

\* \* \* \* \*